(12) United States Patent
Yoshikawa et al.

(10) Patent No.: US 9,165,363 B2
(45) Date of Patent: Oct. 20, 2015

(54) IMAGE DIAGNOSTIC DEVICE AND IMAGE CORRECTION METHOD

(75) Inventors: Hideki Yoshikawa, Tokyo (JP); Takashi Azuma, Tokyo (JP)

(73) Assignee: HITACHI MEDICAL CORPORATION, Tokyo (JP)

( * ) Notice: Subject to any disclaimer, the term of this patent is extended or adjusted under 35 U.S.C. 154(b) by 47 days.

(21) Appl. No.: 14/236,347

(22) PCT Filed: Jul. 24, 2012

(86) PCT No.: PCT/JP2012/068646
§ 371 (c)(1),
(2), (4) Date: Mar. 21, 2014

(87) PCT Pub. No.: WO2013/018575
PCT Pub. Date: Feb. 7, 2013

(65) Prior Publication Data
US 2014/0193099 A1    Jul. 10, 2014

(30) Foreign Application Priority Data
Aug. 3, 2011 (JP) .................................. 2011-170133

(51) Int. Cl.
*G06K 9/32* (2006.01)
*G06T 7/00* (2006.01)
(Continued)

(52) U.S. Cl.
CPC .............. *G06T 7/003* (2013.01); *A61B 6/5235* (2013.01); *A61B 6/5241* (2013.01); *A61B 8/5246* (2013.01); *A61B 5/055* (2013.01);
(Continued)

(58) Field of Classification Search
None
See application file for complete search history.

(56) References Cited

U.S. PATENT DOCUMENTS

| 4,870,692 A | * | 9/1989 | Zuiderveld et al. | ........... 382/107 |
| 5,633,951 A | * | 5/1997 | Moshfeghi | .................... 382/154 |

(Continued)

FOREIGN PATENT DOCUMENTS

| JP | 5-168626 A | 7/1993 |
| JP | 2000-342558 A | 12/2000 |

(Continued)

OTHER PUBLICATIONS

Deuerling-Zheng et al, Motion compensation in digital subtraction angiography using graphics hardware, Computerized Medical Imaging and Graphics 30 (2006) 279-289.*

(Continued)

*Primary Examiner* — Andrae S Allison
(74) *Attorney, Agent, or Firm* — Baker Botts L.L.P.

(57) ABSTRACT

Provided is an image diagnostic device with which it is possible to correct location misalignment of an image capture subject, and to improve the reliability of the result of the correction, in time series image data. An image diagnostic device may include an input part (13) which receives image data input; a correction unit (14) which computes a correction vector which denotes location misalignment of an image capture subject, and selects image data used with an image correction unit; an image correction part (20) which carries out a correction process on the image data based on the correction vector and creates corrected image data; a control part (21) which controls the correction unit and the image correction part; a memory (22) which stores the corrected image data and measurement data as stored data; an output unit (23) which outputs the stored data externally; a display unit (24) which displays the stored data; and an external input device (30) where an operator makes an input operation.

14 Claims, 15 Drawing Sheets

(51) Int. Cl.
*A61B 6/03* (2006.01)
*A61B 6/00* (2006.01)
*A61B 8/08* (2006.01)
*A61B 5/055* (2006.01)

(52) U.S. Cl.
CPC ............... *A61B 6/032* (2013.01); *A61B 6/461* (2013.01); *A61B 6/469* (2013.01); *A61B 6/481* (2013.01); *A61B 6/486* (2013.01); *A61B 6/5211* (2013.01); *A61B 6/5264* (2013.01); *A61B 6/58* (2013.01); *A61B 8/485* (2013.01); *A61B 8/5207* (2013.01); *A61B 8/5215* (2013.01); *A61B 2576/00* (2013.01); *G06T 2200/24* (2013.01); *G06T 2207/20104* (2013.01); *G06T 2207/30004* (2013.01)

(56) References Cited

U.S. PATENT DOCUMENTS

| | | | | |
|---|---|---|---|---|
| 6,169,817 | B1 * | 1/2001 | Parker et al. | 382/131 |
| 6,757,423 | B1 * | 6/2004 | Amini | 382/154 |
| 6,831,948 | B1 * | 12/2004 | Van Dijk et al. | 375/240.12 |
| 7,440,628 | B2 | 10/2008 | Chefd'hotel | |
| 8,460,191 | B2 | 6/2013 | Yoshikawa et al. | |
| 8,873,823 | B2 * | 10/2014 | Koehler et al. | 382/131 |
| 9,025,844 | B2 * | 5/2015 | Iwase et al. | 382/131 |
| 2006/0045366 | A1 * | 3/2006 | Chefd'hotel | 382/236 |
| 2007/0260137 | A1 * | 11/2007 | Sato et al. | 600/407 |
| 2008/0037845 | A1 * | 2/2008 | Deuerling-Zheng et al. | 382/130 |
| 2012/0269438 | A1 * | 10/2012 | Kutsumi | 382/182 |

FOREIGN PATENT DOCUMENTS

| | | |
|---|---|---|
| JP | 2005-204282 A | 7/2005 |
| JP | 2005-323994 A | 11/2005 |
| JP | 2009-369 A | 1/2009 |
| JP | 2009-112468 A | 5/2009 |
| JP | 2011-500250 A | 1/2011 |
| WO | 2006/026177 A1 | 3/2006 |
| WO | 2006/123742 A1 | 11/2006 |
| WO | 2009/053896 A2 | 4/2009 |

OTHER PUBLICATIONS

Meijering, E.H.W.; Zuiderveld, K.J.; Niessen, W.J.; Viergever, M.A., "A fast image registration technique for motion artifact reduction in DSA," Image Processing, 1999. ICIP 99. Proceedings. 1999 International Conference on , vol. 3, no., pp. 435,439 vol. 3, 1999.*

* cited by examiner

FIG. 10
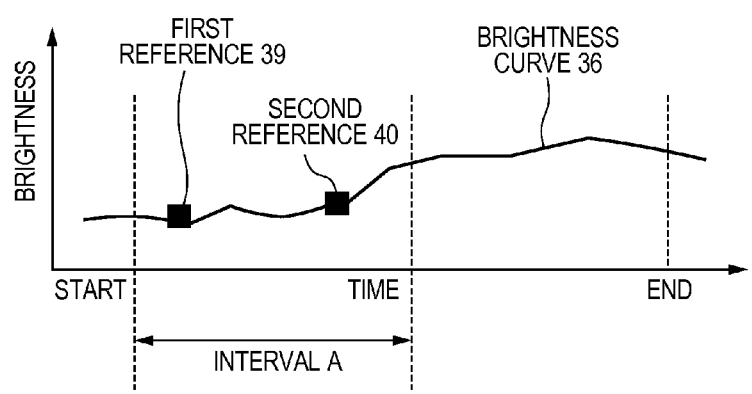
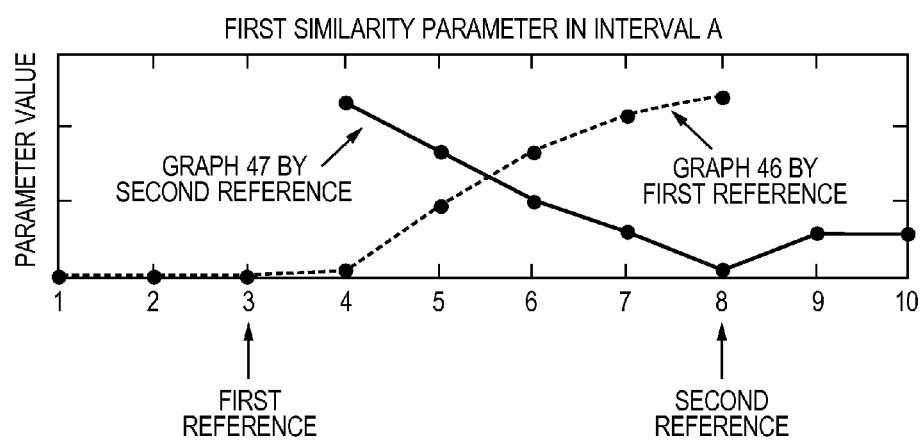

IMAGE DIAGNOSTIC DEVICE AND IMAGE CORRECTION METHOD

TECHNICAL FIELD

The present invention relates to an image process for correcting the positional shift of an imaging target for time-series image data, and particularly to an image correction technique for evaluating the reliability of a correction result to realize a correction process.

BACKGROUND ART

A technique of a time-series image process in which an image process of addition or subtraction is performed for plural pieces of image data obtained in different time phases and temporal changes of an imaging target are extracted has been widely used in various fields. Especially, with the advanced performance of devices in the medical image diagnostic field, attention has been paid to technical development relating to not only a technique of imaging the shape of tissue that has been the mainstream, but also a function evaluation technique of evaluating the property of tissue. In the ultrasonic diagnosis, the imaging time of an image is shorter as compared to an MRI (Magnetic Resonance Imaging) device or a CT (Computed Tomography), and temporal changes can be captured in fine temporal resolution. Therefore, a function evaluation by the time-series image process is especially effective, and many manufacturers have proposed characteristic function evaluation techniques. For example, a technique of estimating the hardness of cancer in such a manner that tissue of interest is compressed from the body surface and the distortion amount of the tissue is calculated on the basis of image data before and after the compression has be used mainly in the breast cancer diagnostic field. Further, in the contrast diagnostic field, there has been widely known a technique in which a process of selecting the maximum brightness is performed on a pixel basis for a series of image data obtained in a process in which a contrast dye flows into tissue of interest and vascular distribution is highlighted.

An important technique in such a time-series image process is a technique of correcting the positional shift of an imaging target occurring between the pieces of image data. In the medical field, an opportunity for obtaining image data is limited due to the burden on patients and the procedure of applying a contrast dye, and thus it is important how the effect of the positional shift is eliminated from the obtained image data. For example, Patent Literature 1 and Patent Literature 2 are related prior arts.

In the correction technique of Patent Literature 1, the resolution of image data to be corrected is reduced to obtain characteristic information using a Laplacian filter. Using the characteristic information, the movement between the pieces of image data is corrected. In the correction technique of Patent Literature 2, image data to be corrected is divided into plural areas, and a correction amount is measured for each area, so that body motion components including deformation of the target are evaluated.

CITATION LIST

Patent Literature

Patent Literature 1: WO 2006/026177
Patent Literature 2: WO 2006/123742

SUMMARY OF INVENTION

Technical Problem

As described above, in the process of correcting the positional shift of the imaging target for the time-series image data, especially in the process of correcting the positional shift caused by body motion, the accuracy of correction is highly important. Patent Literature 1 is effective in improving the correction accuracy, and Patent Literature 2 is effective in improving the correction accuracy for deformation. However, a mechanism of evaluating the accuracy of the correction result is not provided in any of the techniques. In the time-series image process, a unique correction error on the time series exposes an unnatural structure pattern on the result image, and the quality of the image is deteriorated in many cases as compared to a case in which no correction process is performed. Thus, in the time-series image process, a mechanism of evaluating the reliability of the result is essential in addition to the high accuracy of the correction.

In order to address the above-described problems, an object of the present invention is to provide an image diagnostic device and an image correction method that can realize the high accuracy of correction, and can evaluate the reliability of a result.

Solution to Problem

In order to achieve the above-described object, the present invention provides an image diagnostic device that corrects time-series image data, the device including: a correction unit that selects image data to be corrected from the time-series image data on the basis of a similarity to a reference image and outputs correction vectors representing the positional shift of the selected image data; an image correction unit that performs a correction process for the image data on the basis of the correction vectors to create corrected image data; and a display unit that displays an image on the basis of the corrected image data.

Further, in order to achieve the above-described object, the present invention provides the image diagnostic device, wherein the correction unit includes: an area setting unit that sets an area where the correction process is performed for the time-series image data; a reference setting unit that sets a reference image from the time-series image data; a first similar area search unit that searches the image data for an area similar to the reference image and outputs a similarity value indicating the similarity; a similarity evaluation unit that generates a similarity parameter for evaluating the similarity value; and an image selection unit that selects the image data used in the image correction unit on the basis of the similarity parameter.

Further, in order to achieve the above-described object, the present invention provides the image diagnostic device, wherein a deformation correction unit is further provided, and the deformation correction unit includes an area division unit that divides the area where the correction process set by the correction unit is performed to set plural divided areas, a second similar area search unit that searches the plural divided areas for the area similar to the reference image to calculate the correction vectors, and an error correction unit that performs error correction for the correction vectors calculated by the second similar area search unit.

Furthermore, the present invention provides an image correction method in which a processing unit corrects time-series image data, wherein the processing unit selects image data to be corrected from the time-series image data on the basis of a similarity to a reference image, calculates correction vectors indicating the positional shift of the selected image data, and performs a correction process for the image data on the basis of the correction vectors to create corrected image data.

Advantageous Effects of Invention

According to the present invention, it is possible to provide an image diagnostic device and an image correction method that can realize the high accuracy of correction, and can evaluate the reliability of a result.

BRIEF DESCRIPTION OF DRAWINGS

FIG. 10 is a diagram for explaining a process of a vector connection unit of the image diagnostic device of the first embodiment.

DESCRIPTION OF EMBODIMENTS

Figure 1:
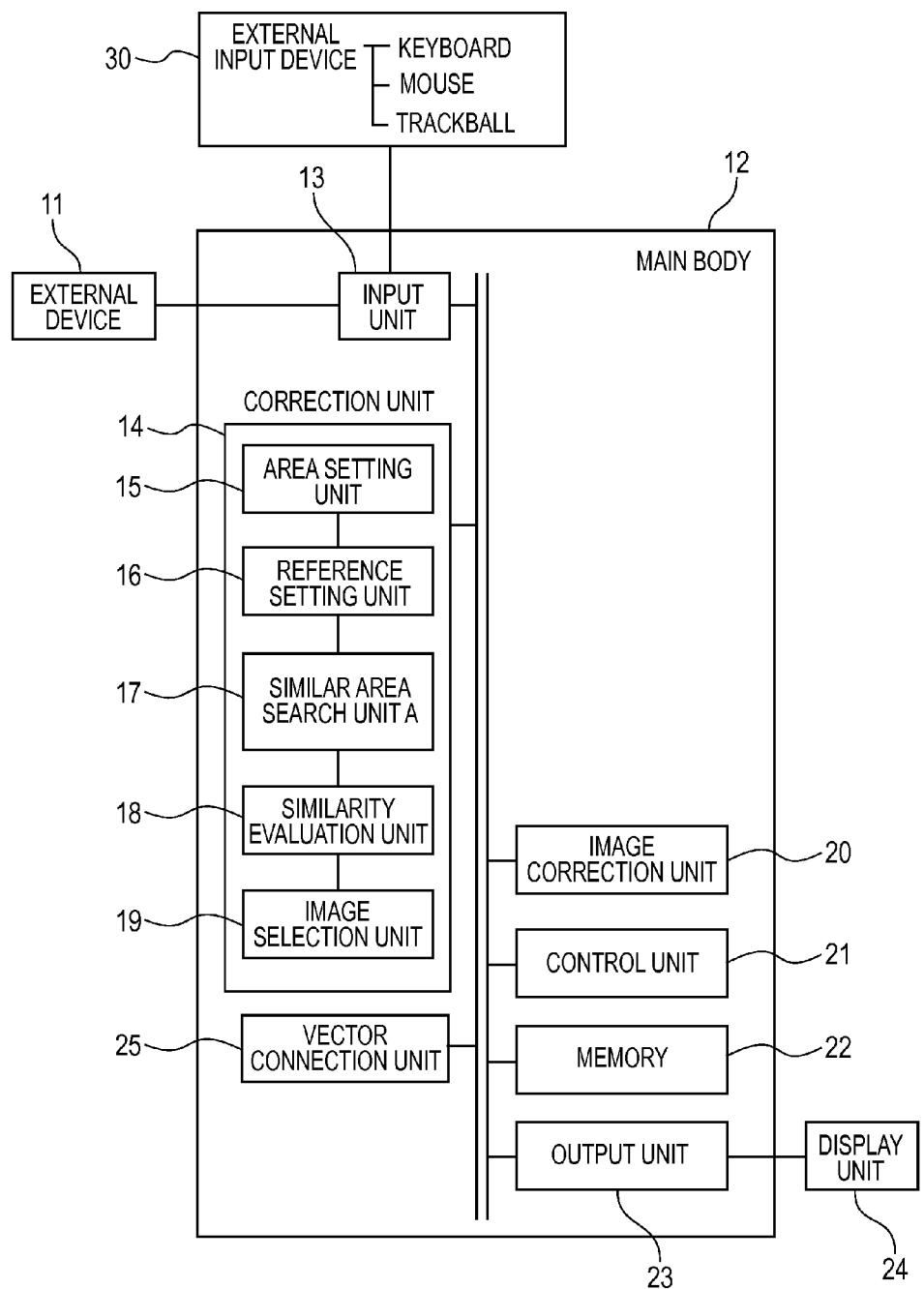
FIG. 1 is a block diagram for showing a configuration example of an image diagnostic device of a first embodiment.

Hereinafter, embodiments of the present invention will be described in accordance with the drawings. It should be noted that a correction process of a position is performed while the movement of an imaging target is assumed as rigid motion in the description. The "rigid" indicates an object that is not deformed, and the rigid motion means motion in which movement in each position in the object is translation movement. Further, a reference image is image data serving as a reference in the correction process, and is set on the basis of time-series image data input into the device. A similar area means an area similar to the reference image. Further, a similarity indicates a degree at which pieces of data in two areas match each other. A similarity value is a value to evaluate the similarity, and is calculated in a search process for the similar area. A similarity value map is a two-dimensional map configured using the all similarity values calculated in the search process, and a two-dimensional map obtained by applying an edge emphasis filter to the similarity value map is referred to as a similarity value distribution map. In addition, a similarity parameter is a value to evaluate the reliability of a search result.

First Embodiment

Hereinafter, a configuration example of an image diagnostic device of a first embodiment will be described using FIG. 1 to FIG. 11. The first embodiment relates to an image diagnostic device that can correct a positional shift of an imaging target for time-series image data from an external device to improve the reliability of the correction result. Specifically, the first embodiment relates to an image diagnostic device that corrects time-series image data, and is an embodiment of an image diagnostic device including a correction unit 14 that selects image data to be corrected from the time-series image data on the basis of the similarity to the reference image and outputs correction vectors indicating the positional shift of the selected image data, an image correction unit 20 that performs a correction process for the image data on the basis of the correction vectors to create corrected image data, and a display unit 24 that displays an image on the basis of the corrected image data. Further, the first embodiment relates to an image correction method in which the time-series image data is corrected by a processing unit in a main body 12, and is an embodiment of an image correction method in which the processing unit selects image data to be corrected from the time-series image data on the basis of the similarity to the reference image to calculate correction vectors indicating the positional shift of the selected image data, a correction process is performed for the image data on the basis of the correction vectors to create corrected image data, and an image on the basis of the corrected image data is displayed on a display unit.

In the embodiment, the correction unit 14 includes an area setting unit 15 that sets an area where the correction process is performed for the time-series image data, a reference setting unit 16 that sets the reference image from the time-series image data, a first similar area search unit 17 that searches the image data for an area similar to the reference image and outputs the similarity value representing the similarity, a similarity evaluation unit 18 that generates the similarity parameter for evaluating the similarity value, and an image selection unit 19 that selects the image data used in the image correction unit on the basis of the similarity parameter.

FIG. 1 shows a functional block diagram of the image diagnostic device of the first embodiment. The image diagnostic device of the first embodiment includes an external device 11 that obtains the image data, a main body 12 that performs the correction process for the image data, a display unit 24 that displays information output from the main body 12, and an external input device 30. The main body 12 includes an input unit 12 that inputs the image data, a correction unit 14 that performs the correction process using the image data while assuming the movement of the imaging target as rigid motion to output the correction vectors, an image correction unit 20 that corrects the image data using the correction vectors to create and output the corrected image data, a control unit 21 that controls the main body 12, a memory 22 that stores the image data and measured data as stored data, an output unit 23 that outputs the image data and the measured data such as the corrected image data that are stored in the memory 22 and created by the main body 12, and a vector connection unit 25.

The correction unit 14 includes an area setting unit 15 that sets an area where the correction process is performed for the image data input into the input unit 13, a reference setting unit 16 that sets the reference image serving as a reference in the correction process from the image data, a similar area search unit A 17 that searches the target image data for a similar area similar to the reference image to calculate the correction vectors, a similarity evaluation unit 18 that evaluates the result of the similar area search unit A 17, and an image selection unit 19 that selects the image data used in the image correction unit 20 on the basis of the result of the similarity evaluation unit 18.

The external device 11 supposedly obtains ultrasonic image data, MRI image data, and CT image data from a medical image diagnostic device such as an ultrasonograph, an MRI device, or a CT device. However, the image diagnostic device of the embodiment can be applied to general image data irrespective of the kind of the external device such as a digital camera or a CCD camera. Further, the external input device 30 is, for example, a keyboard, a mouse, a trackball, or the like, and an operator can input necessary commands or data into the main body 12 using the external input device 30.

Of the above-described functional blocks, the vector connection unit 25 has a function of connecting the results of the correction vectors calculated on the basis of the respective reference images when there are plural reference images set by the reference setting unit 16 of the correction unit 14. Thus, when the number of reference images is one, it is not necessary to use the vector connection unit 25.

The main body 12 of the image diagnostic device of the embodiment can be realized using a normal computer device. Specifically, the normal computer device is configured using a CPU (Central Processing Unit), a memory as a storage unit, and an input/output interface as an input/output unit. Of the functional blocks in the main body 12 of FIG. 1, the input unit 13 and the output unit 23 correspond to the input/output interface, the memory 22 corresponds to the memory, and the control unit 21 corresponds to the CPU. Further, the correction unit 14, the vector connection unit 25, and the image correction unit 20 as the functional blocks correspond to functional programs that are stored in the memory 22 and executed by the CPU. Further, the display unit 24 and the external input device 30 correspond to a display and a keyboard accompanied by the computer device. In the description, the correction unit 14, the image correction unit 20, the control unit 21, and the vector connection unit 25 are collectively referred to as a processing unit in some cases.

Next, a process of the correction unit 14 of the device in the embodiment will be described in accordance with the flowchart shown in FIG. 2. Each processing step of the flowchart can be realized using a program executed by the CPU except the input/output process.

Figure 3:
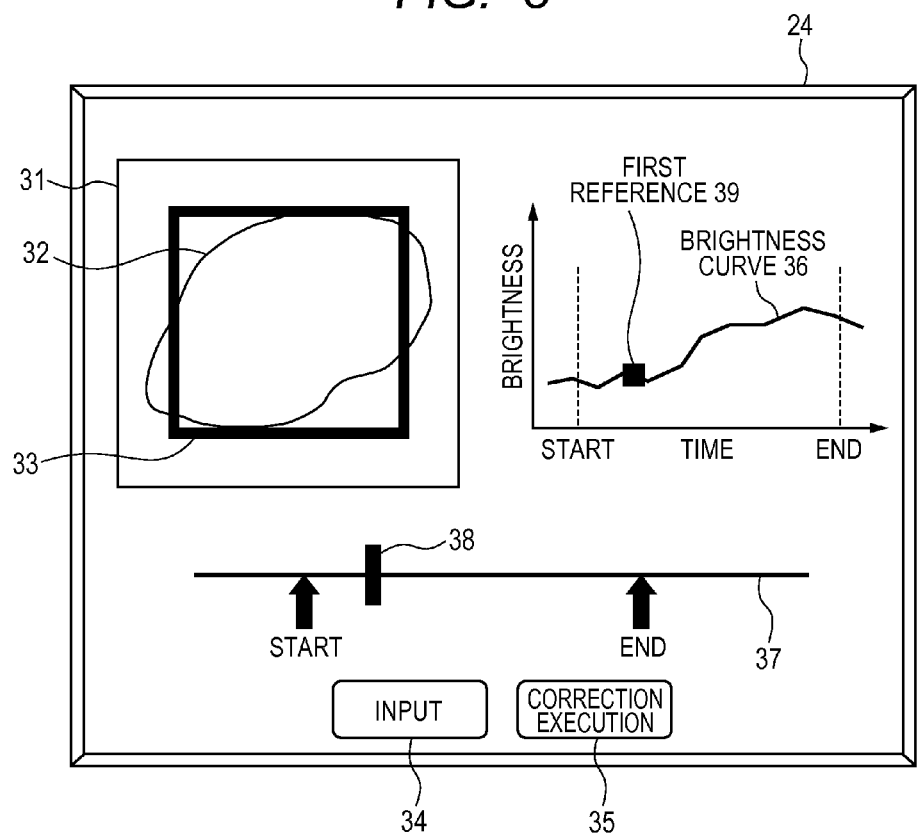
FIG. 3 is a diagram for showing an example of a display configuration when a processing range of the image diagnostic device of the first embodiment is set.

First, a setting of a processing range in Step 1 performed in the area setting unit 15 of the correction unit 14 will be described. The processing range includes a time range and an image range as will be sequentially described below. When the image data to be corrected is input into the input unit 13 from the external device 11, exemplified image data 31 among the image data, an input button 34, and a correction execution button 35 are displayed on the display unit 24 as shown in FIG. 3. Further, a brightness curve 36 representing time changes in the average brightness of the exemplified image data 31 is displayed as shown in FIG. 3. At a lower part of the display screen of the display unit 24, provided are a gauge 37 for showing the time range of the image data and a marker 38 for changing the exemplified image data 31. The operator can freely change the exemplified image data 31 on the gauge 37 by moving the marker 38 using the external input device 30.

The time range where the correction process is performed is set using the marker 38. When the operator operates the marker 38 to select the input button 34 at a desired point, the start position is fixed, and an arrow indicating the start position is displayed on the gauge 37. As similar to the above, the end position is fixed. The position of the time indicated by the marker 38 is also displayed on the brightness curve 36, and thus the operator can fix the start and end positions by referring to the exemplified image data 31 and the brightness curve 36. Further, the fixed start and end positions are displayed on the display unit 24 in the form shown in FIG. 3.

The image range where the correction process is performed is set in the area setting unit 15 using a processing area 33 displayed as a rectangular frame displayed on the exemplified image data 31. When the operator adjusts the position and range of the processing area 33 in the image data 31 using the external input device 30 to select the input button 34, the processing area 33 as the image range where the correction process is performed is fixed. Along with the changes in the position and range of the processing area 33, the brightness curve 36 displayed on the display unit 24 is immediately changed.

Next, a first reference image for the correction process in Step 2 is set in the reference setting unit 16. As described above, the reference image is image data serving as a reference in the correction process. When the processing area 33 is fixed in Step 1, a mark 39 indicating the position of the first reference image is displayed on the brightness curve 36. The position of the mark 39 corresponds to that of the marker 38 on the gauge 37. The input button 34 is selected at a desired position while moving the marker 38 on the gauge 37, so that the first reference image is fixed. It should be noted that the initial position of the marker 38 is set at the start position of the time range set in Step 1 in the process of Step 2.

When the first reference image is fixed by selecting the input button 34, a mark indicating the position of a second reference image (not shown) is similarly displayed on the brightness curve 36. A case in which plural reference images are set will be described later. It should be noted that setting methods after the second reference image are the same as those of the first reference image, and are repeated until the operator selects the correction execution button 35 displayed on the display unit 24. In the case where the correction execution button 35 is selected after the first reference image is fixed, the number of reference images becomes only one.

Next, a search for a similar area in Step 3 is performed in the similar area search unit A 17. First, a case of one reference image will be described.

Here, the terms used in the following description will be defined. As described above, the similarity indicates a degree at which the similar area as the search result matches the processing area. The processing area is an area to be processed in the reference image. The similarity value is a value for evaluating the similarity, and is a value calculated in the search process for the similar area performed by the similar area search unit A 17 and a similar area search unit B to be described in a second embodiment. The similarity value map is a two-dimensional map configured using the all similarity values calculated in the search process. For example, in the case where the similar area is searched for by residual estimation in the method of least squares, the position of the minimum value on the similarity value map is evaluated as the highest similarity. Further, the two-dimensional map obtained by applying the edge emphasis filter to the similarity value map is regarded as the similarity value distribution map. Further, the value used to evaluate the reliability of the search result is selected from the similarity value map or the similarity value distribution map to be regarded as the similarity parameter.

Figure 4:
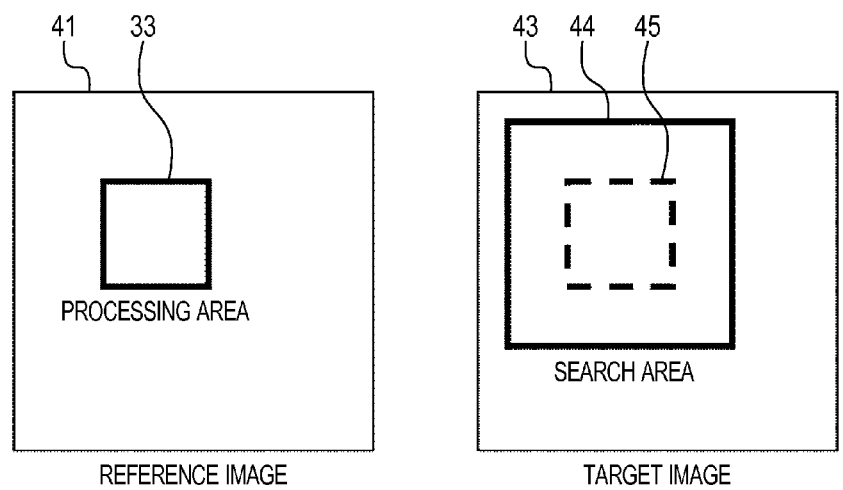
FIG. 4 is a diagram for explaining a search for a similar area according to the first embodiment.
Figure 5:
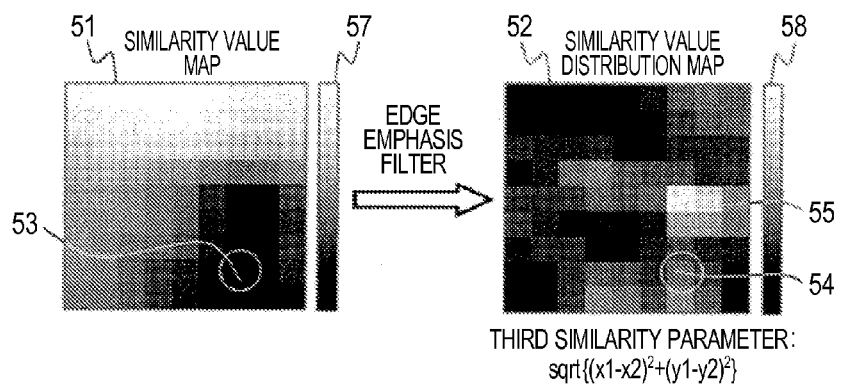
FIG. 5 is a diagram for explaining the content of a similarity parameter according to the first embodiment.

FIG. 4 is a schematic view for explaining a relation between the reference image and the target image in the search for the similar area, and the search for the similar area in the similar area search unit A 17 of the main body 12 will be described with reference to FIG. 4. The search for the similar area in the similar area search unit A 17 is performed between the processing area 33 on a reference image 41 in the first reference 39 set in Step 1 and all the image data except the reference image 41 in the time range set in Step 1. Hereinafter, the image data where the similar area is searched for is referred to as the target image. As shown in FIG. 4, a search area 44 that has the center same as the processing area 33 and is enlarged by a range (hereinafter, assumed as S) that is preliminarily set by the operator in four directions of the processing area 33 is provided on a target image 43. An area 45 represented by the dotted line of FIG. 4 indicates the position of the processing area 33 on the target image 43. An area having a size same as the processing area 33 is extracted from the search area 44 to perform an operation for calculating the similarity value. The area to be extracted is moved by one pixel, and an operation is performed at the moved position, so that a similarity value map 51 having a size of (2S+1)×(2S+1) shown on the left side of FIG. 5 is created. In FIG. 5, the reference numeral 57 denotes a gray scale. It should be noted that a concrete example of calculating the similarity value that is a value to evaluate the similarity will be described later.

It should be noted that when the similarity value map 51 is created in the embodiment, the processing time can be shortened by reducing the pixels to be searched for. When reducing the pixels, an LPF (Low-Pass Filter) is first applied to the reference image 41 and the target image 43. The size of the LPF is substantially the same as the number of pixels to be reduced. For example, the search is performed for every two pixels, a 2×2 LPF is applied. In this case, the size of the similarity value map is (S+1)×(S+1). The position of the minimum value is calculated from the similarity value map, so that the correction vectors having errors corresponding to the reduced two pixels are fixed. Next, the similar area is searched for again near the position of the correction vectors that is the position of the minimum value of the similarity value map. The purpose of this process is to correct the errors. Thus, the LPF is not applied to the reference image 41 and the target image 43, and the pixels are not reduced. By performing the above-described process, the final correction vectors are calculated.

Figure 6:
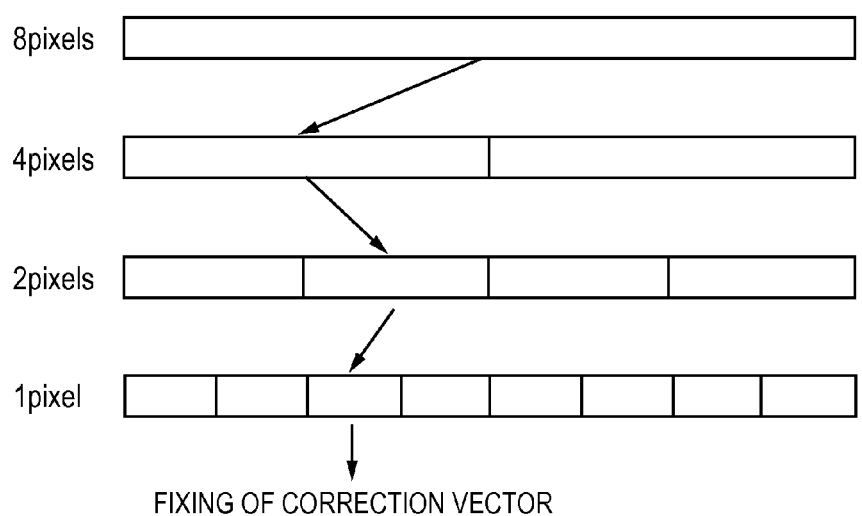
FIG. 6 is a diagram for explaining a high-speed process according to the first embodiment.

FIG. 6 is a diagram for schematically showing a high-speed operation by the above-described reduction process and the included errors. As shown in the drawing, the process is a process in which the accuracy of the correction vectors to be calculated is increased in stages. In the aforementioned example, the first search is performed with the accuracy of two pixels, and the second search is performed with the accuracy of one pixel. By increasing the number of pixels to be reduced, the number of times of operations of the similarity value performed in the first search can be further reduced. However, the number of times of re-searches performed to correct the errors corresponding to the number of reduced pixels is increased, and the effect obtained by shortening the operation time becomes low.

Figure 7:
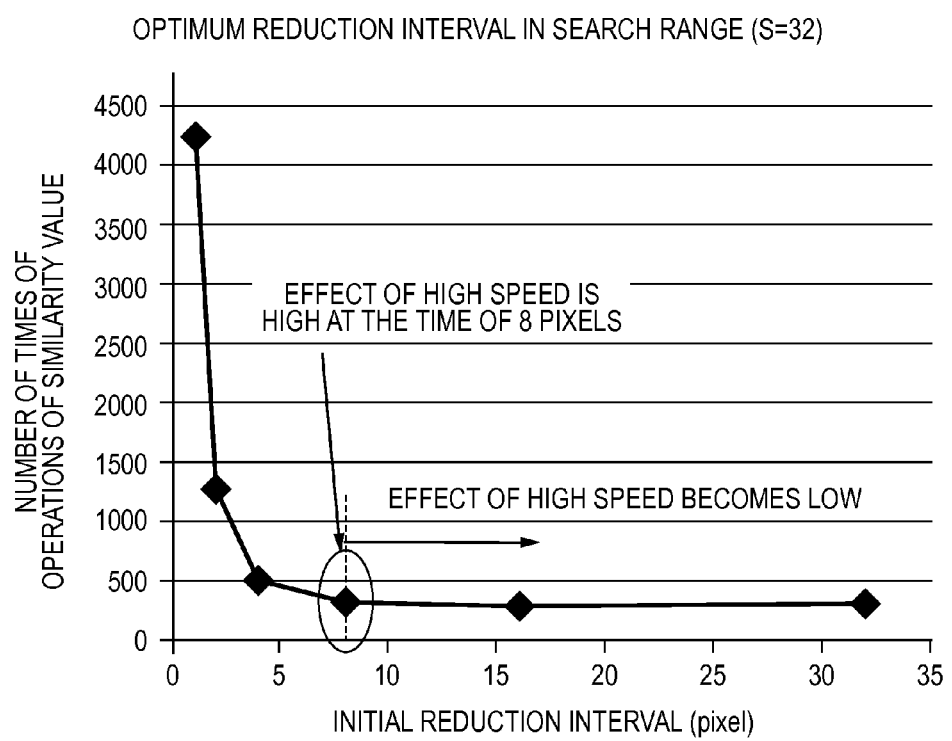
FIG. 7 is a diagram for explaining an effect of the high-speed process according to the first embodiment.

FIG. 7 shows an example of a relation between the reduction interval and the number of times of operations of the similarity value. As being apparent from the drawing, the effect of the high-speed operation by the reduction process is apparent. For example, in the case of S=32, it can be determined that the optimum reduction interval is 8 pixels.

It should be noted that the operation to calculate the similarity value in the similar area search unit A 17 indicates a method of obtaining a residual error between images or a method represented by the cross-correlation operation that is represented by the sum of squared differences or the sum of absolute differences. In the method using the residual error, the position of the minimum value on the similarity value map is detected as the highest similarity area. In the method using the correlation operation, the position of the maximum value on the similarity value map is detected as the highest similarity area. As shown in FIG. 4, the center position of the search area 44 is the same as that of the processing area 33. Thus, in the case where the amount of movement between the pieces of image data where the similarity value is calculated is 0, the highest similarity position is the center of the similarity value map. Thus, the vector connecting the center position of the similarity value map to the position where the similarity is high is the correction vector in the embodiment. Hereinafter, the explanation of the embodiment will be continued on the assumption that the method using the residual error is used and the position of the minimum value on the similarity value map is the highest similarity area.

The similar area search unit A 17 outputs the similarity value map 51 and the correction vectors as the search result. After the search for the similar area in Step 3 is executed in the similar area search unit A 17, the calculation of the similarity parameter in Step 4 is performed using the similarity value map 51 generated by the similar area search unit A 17 in the similarity evaluation unit 18 of the correction unit 14. In the embodiment, a first similarity parameter is defined using the minimum value on the similarity value map. In the case of FIG. 5, a minimum value 53 on the similarity value map 51 is the first similarity parameter. While the position of the minimum value 53 on the similarity value map 51 is represented as (x1, x2), the first similarity parameter is represented as I1(x1, y1).

Next, the edge emphasis filter is applied to the similarity value map 51 in the similarity evaluation unit 18 to create a similarity value distribution map 52 shown on the right side of FIG. 5. As an example of the edge emphasis filter, a Laplacian filter is used. The effect of applying the edge emphasis filter in the similarity evaluation unit 18 is to improve the reliability of the similarity evaluated on the similarity value map 51. It should be noted that the reference numeral 58 in FIG. 5 denotes a gray scale.

Figure 8:
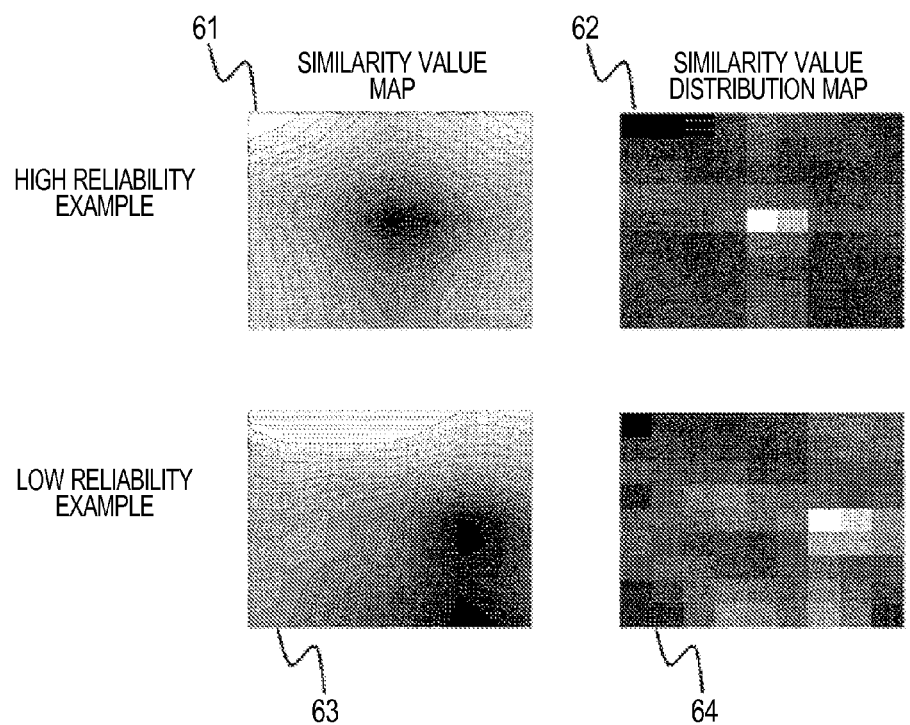
FIG. 8 is a diagram for explaining the meaning of the similarity parameter according to the first embodiment.

FIG. 8 shows similarity value maps 61 and 63 of two examples of a high reliability example and a low reliability example, and similarity value distribution maps 62 and 64 that are results obtained by applying the edge emphasis filter to each of the similarity value maps 61 and 62. The similarity value maps 61 and 62 are expressed using contour drawings in accordance with values. On the similarity value maps 61 and 63 and the similarity value distribution maps 62 and 64, the magnitudes of the values are expressed using white and black colors. On the similarity value map 61 of a high reliability example, the contour density at the position representing the minimum value is high and local. On the contrary, on the similarity value map 63 of a low reliability example, the contour density at the position representing the minimum value is expanded. As described above, the similarity is evaluated using the minimum value on the similarity value map in the similarity evaluation unit 18 of the embodiment. However, in the case where there are many positions having values nearly equal to the minimum value, the reliability of the evaluation result is deteriorated. In the contour drawing, the contour density near the minimum value suggests distribution of the similarity. As the density becomes higher, the minimum value is local, leading to a highly-reliable result.

The similarity value distribution map calculated in the similarity evaluation unit 18 is used for a method of evaluating the contour density, and the edge emphasis filter is useful as means for evaluating the contour density. As the contour density becomes higher, the larger values are displayed on the similarity value distribution map. In FIG. 8, on the similarity value distribution map 62 of the high reliability example and the similarity value distribution map 64 of the low reliability example, the positions where the contour densities are high are definitely represented by large values (white color). Especially, in the low reliability example, the position of the minimum value is unclear on the similarity value map 63. However, differences are shown using information suggesting the distribution of the similarity shown on the similarity value distribution map 64.

As the Laplacian filter that is an example of the edge emphasis filter, a 4-neighbor Laplacian filter using 4 pixels adjacent to a pixel of interest or an 8-neighbor Laplacian filter using all pixels adjacent to a pixel of interest is used. The optimum size of the filter to evaluate the contour density differs depending on the structure of the brightness pattern included in the processing range 33, the brightness distribution of the minimum unit configuring the image data, and the pixel size of the image data.

For example, in the case of an ultrasonograph, a speckle size is used as the minimum unit configuring the image data. The speckle size is determined in accordance with imaging conditions such as the aperture, frequency, and depth of a device that irradiates ultrasonic waves. In the case where the processing range 33 is nearly equal to the speckle size, the contour density cannot be evaluated by a 4-neighbor or 8-neighbor filter in principle unless the similarity value map is created using moving steps exceeding the speckle size because the difference between the values of adjacent pixels on the similarity value map is small. In this case, it is necessary to expand the pixel size of the similarity value map or the filter size. However, since the brightness pattern of generally-captured image data of an abdominal region or a mammary gland region is complex and the set processing range 33 is substantially large as compared to the speckle size, the contour density can be evaluated with the edge emphasis filter using adjacent pixels.

A second similarity parameter in the embodiment is defined as a value on the similarity value distribution map corresponding to the position of the minimum value on the similarity value map. In the case of FIG. 5, the second similarity parameter is a value 54 on the similarity value distribution map 52 corresponding to the position of the minimum value on the similarity value map 51. In this case, while the position of the value 54 is represented as (x1, y1), the second similarity parameter is represented as I2(x1, y1).

Further, a third similarity parameter is defined as a distance between the position of the minimum value on the similarity value map and the position of the maximum value on the similarity value distribution map. In the case of FIG. 5, the third similarity parameter is a distance between the position of the minimum value 53 on the similarity value map 51 and the position of the maximum value 55 on the similarity value distribution map 52. Namely, while the position of the maximum value 55 on the similarity value distribution map 52 is represented as (x2, y2), the third similarity parameter is represented as a distance of sqrt$\{(x1-x2)^2+(y1-y2)^2\}$.

It is obvious that in the case where the correlation operation is used as a method of calculating the similarity value, the similarity parameter can be calculated by inversely changing the indexes of the maximum value and the minimum value used on the similarity value map and the similarity value distribution map.

Of the results obtained by the similarity evaluation unit 18, the most reliable result is when the third similarity parameter is 0. As described above, the usage of the similarity value distribution map 52 means that the contour density of the similarity value map 51 is evaluated. Therefore, it is not always necessary to evaluate the contour density around the minimum value on the similarity value map, but I2(x2, y2) is located around the maximum value on the similarity value map in some cases. Thus, when the reliability is evaluated, it is more effective to perform a process of extracting an area having a value half or smaller the threshold value that is preliminarily set for the similarity value map, for example, the maximum value or the minimum value on the similarity value map to use I2(x2, y2) in the area for the calculation of the similarity parameter.

It should be noted that as the similarity parameter calculated by the similarity evaluation unit 18, other statistics calculated using the similarity value map than the above-described similarity parameters 1, 2, and 3 are useful. For example, the statistics include the standard deviation of the similarity value map and a preliminarily-set threshold value, for example, the number of pixels half or smaller the maximum value or the minimum value on the similarity value map.

Figure 2:
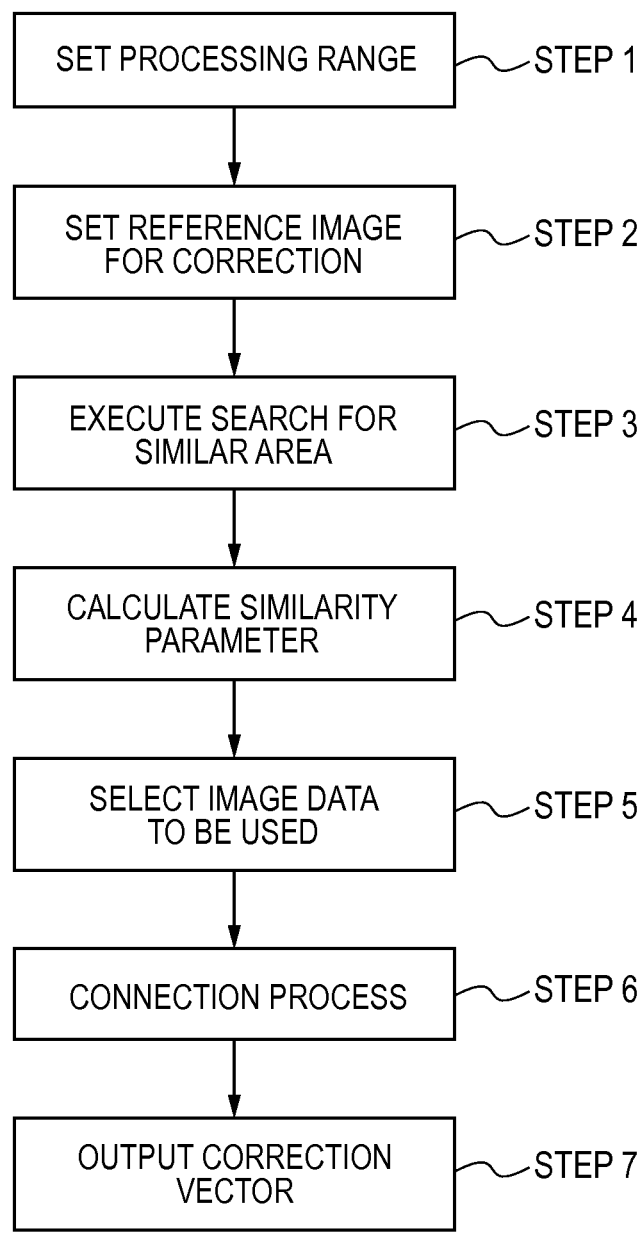
FIG. 2 is a diagram for explaining an example of processing steps of the image diagnostic device of the first embodiment.
Figure 9A:
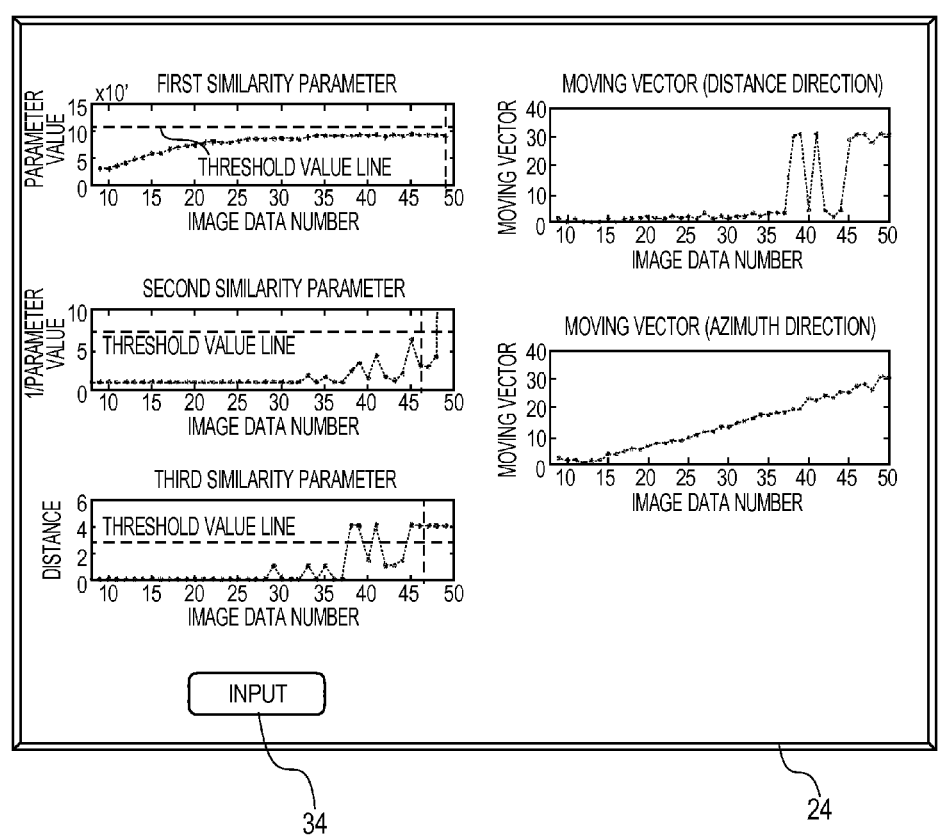
FIG. 9A is a diagram for showing an example of display when an image is selected in the image diagnostic device of the first embodiment.

When the similarity parameter is calculated by the similarity evaluation unit 18, the image data to be used is selected in Step 5 of FIG. 2. Specifically, the image data to be used by the image correction unit 20 is selected by the image selection unit 19 of the correction unit 14. The image diagnostic device of the embodiment is set in such a manner that the first, second, and third similarity parameters output from the similarity evaluation unit 18 are displayed on the display unit 24 in the form shown in FIG. 9A when each similarity parameter is calculated in Step 4. However, as being apparent from the drawing, the second similarity parameters are displayed using a graph of the inverse numbers of the values, and the tendency in which the smaller the value is, the higher the reliability is standardized in the all similarity parameters. The content to be displayed can be freely selected by the operator. For example, only the third similarity parameters can be displayed. Further, the moving vectors in the distance direction (the vertical direction of the image data) and the azimuth direction (the horizontal direction of the image data) representing the correction vectors calculated on the basis of the position of the minimum value on the similarity value map in the similar area search unit A 17 are displayed on the display unit 24. The horizontal axis of each graph in FIG. 9A represent an image data number in the time range set by the area setting unit 15. Instead of the image data number, the time range itself set by the area setting unit 15 may be set on the horizontal axis.

A threshold value line for setting threshold values represented by the dotted line is provided on each graph of the similarity parameters of FIG. 9A. The operator sets the threshold values for the respective similarity parameters, and outputs the image data and the correction vectors under the threshold value line as data to be used in the correction process. As the initial value of each threshold value line, the maximum value of each similarity parameter is used, and all correction vectors are used at an early stage. The change of the threshold value line is promptly reflected on each graph of the correction vectors. For example, only the correction vectors to be used are displayed by different colors or different marks. When the adjustment of the threshold value line is finished in the image selection unit 19, the operator selects the input button 34, and thus the selection of the image data and the correction vectors for correction used in the image correction unit 20 is completed. The correction vectors calculated by the image selection unit 19 are stored in the memory 22, and output to the image correction unit 20.

Figure 9B:
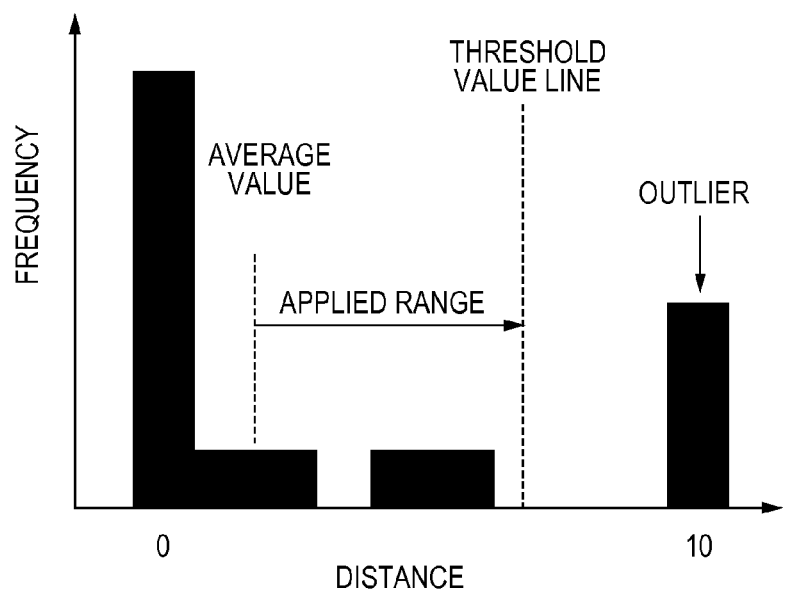
FIG. 9B is a diagram for showing a histogram for selecting an image in the image diagnostic device of the first embodiment.

It should be noted that the threshold value line can be set by changing the configuration of the similarity parameter displayed on the display unit 24 to the configuration of a histogram as shown in FIG. 9B. Further, the threshold value line can be automatically set by statistically processing the similarity parameters. The average value, the distributed value, the standard deviation, and the histogram of the respective calculated similarity parameters are calculated, and the threshold value line is set at the position where outliers are removed. For example, in the histogram of the third similarity parameters shown in FIG. 9B, the threshold value line is automatically set from an applied range determined on the basis of the average value and the standard deviation.

Here, as a modified example of the embodiment, a case in which not only the first reference image but also plural reference images are set by the reference setting unit 16 of the image diagnostic device in the embodiment will be described. The setting of plural reference images is suitable for a case in which the correction process is performed for image data using, for example, a contrast dye. The brightness pattern of the image largely differs before and after injection of the contrast dye. Thus, the reliability of the correction process by a single reference image is deteriorated, and errors of the correction vectors frequently occur. Thus, when setting the reference image for correction in Step 2, the operator can accurately recognize the time changes in the brightness of the processing area 33 and can set the appropriate number of reference images at appropriate locations by referring to the brightness curve shown in FIG. 3.

As shown on the upper side of FIG. 10, a case in which a first reference 39 and a second reference 40 are set in an interval A is simulated. Step 3 and Step 4 of FIG. 2 are performed at each reference. However, the interval where Step 3 and Step 4 are performed ranges from the start position to the second reference 40 for the first reference 39, and ranges from the first reference to the end position for the second reference 40.

The results of the first, second, and third similarity parameters and the correction vectors calculated at the first reference and the second reference are output to the vector connection unit 25, and a connection process of the correction vectors using the similarity parameters are performed (Step 6).

On the lower side of FIG. 10, graphs 46 and 47 of the first similarity parameters at the first reference 39 and the second reference 40 are shown in the range of the interval A. As described above, the smaller the value of the similarity parameter is, the higher the reliability is. Thus, the parameter values on the basis of the first reference and the second reference are compared to each other in the interval A, and the correction vectors calculated by the reference in which the smaller value is used are selected. It should be noted that the connection process may be performed in a combination of the second and third similarity parameters, and the embodiment thereof can be freely selected by the operator. Further, the threshold value line is also provided in the time axis direction, and the time range can be adjusted. It should be noted that the above-described connection process is automatically performed by the vector connection unit 25. Further, the similarity parameters in the interval A are stored in the memory 22, and the operator can appropriately confirm the validity of the connection process on the display unit 24. In the case where the validity is low, the operator can freely change the processing content of the vector connection unit 25.

Next, corrected image data is created in the image correction unit 20 using the image data to be corrected and the correction vectors output from the correction unit 14. The corrected image data to be created is the image obtained by correcting the positional shift of the imaging target in the image data using the correction vectors. Specifically, using the similarity value map obtained from the similar area search unit A 17, the image data of the target image that is evaluated by the similarity evaluation unit 19 and is selected by the image selection unit 19 is moved by the corresponding correction vectors, so that the corrected image data with the rigid motion of the imaging target corrected is created. In this stage, an example 91 of the corrected image data is displayed, and the moving vectors (distance direction) 111 and the moving vectors (azimuth direction) 112 that are correction vectors are displayed along the horizontal axis representing the time axis on the display unit 24 as shown in FIG. 11.

Figure 11:
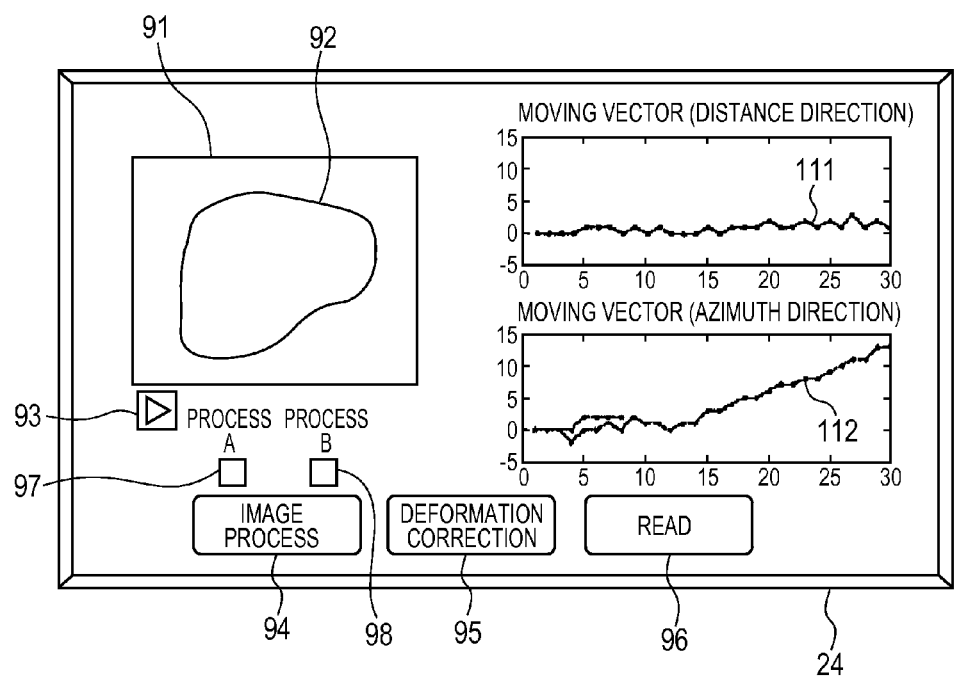
FIG. 11 is a diagram for showing an example of a display configuration of the image diagnostic device of the first embodiment.

As shown in FIG. 11, a reproduction button 93 is further provided on the display unit 24. If the reproduction button 93 is selected using the external input device 30, the corrected image data can be reproduced by a program operation of the control unit 21 in an animated manner. An image processing button 94, a deformation correction button 95, and a read button 96 are further displayed on the display unit 24. The deformation correction button 95 will be described in the second embodiment, and thus the explanation thereof is omitted here.

A process A frame 97 and a process B frame 98 are further provided above the image processing button 94. When a mark is input into the process A frame 97 and the image processing button 94 is selected using the external input device 30, an image process that is preliminarily input in the main body 12, for example, a process of creating an averaging image or a maximum brightness image is executed, and the image after the process is displayed on the display unit 24. This also applies to the process B frame 98. Program sources of various processes corresponding to the process A frame and the process B frame are stored in the memory 22. The operator can not only freely edit, but also increase the types of image processes by adding the process frame.

The read button 96 is used to execute reading of various pieces of image data. While providing a function of reading the correction vectors corresponding to the image data obtained in the past, the similarity parameters, the corrected image data, and the processed images, the read button 96 allows a current result and the image data obtained in the past to be compared to each other on the same screen using a pull-down menu.

Second Embodiment

An image diagnostic device of a second embodiment is configured in such a manner that a deformation correction unit 26 is further provided to the image diagnostic device of the first embodiment and the imaging target can adapt to deformation movement. Specifically, the image diagnostic device of the second embodiment relates to an image diagnostic device having a configuration in which the deformation correction unit 26 is further provided to the image diagnostic device of the first embodiment, and the deformation correction unit 26 includes an area division unit 27 that divides an area where the correction process set by the correction unit 14 is performed and sets plural divided areas, a second similar area search unit 28 that searches for an area similar to the reference image to calculate the correction vectors for the plural divided areas, and an error correction unit 29 that performs error correction for the correction vectors calculated by the second similar area search unit 28.

The image diagnostic device of the second embodiment will be described using FIG. 12 to FIG. 16. It should be noted that another similar area search unit B is used in the embodiment. For the purpose of avoiding confusion, the similar area search unit A and the similar area search unit B are referred to as a first similar area search unit and a second similar area search unit, respectively, in some cases.

Figure 12:
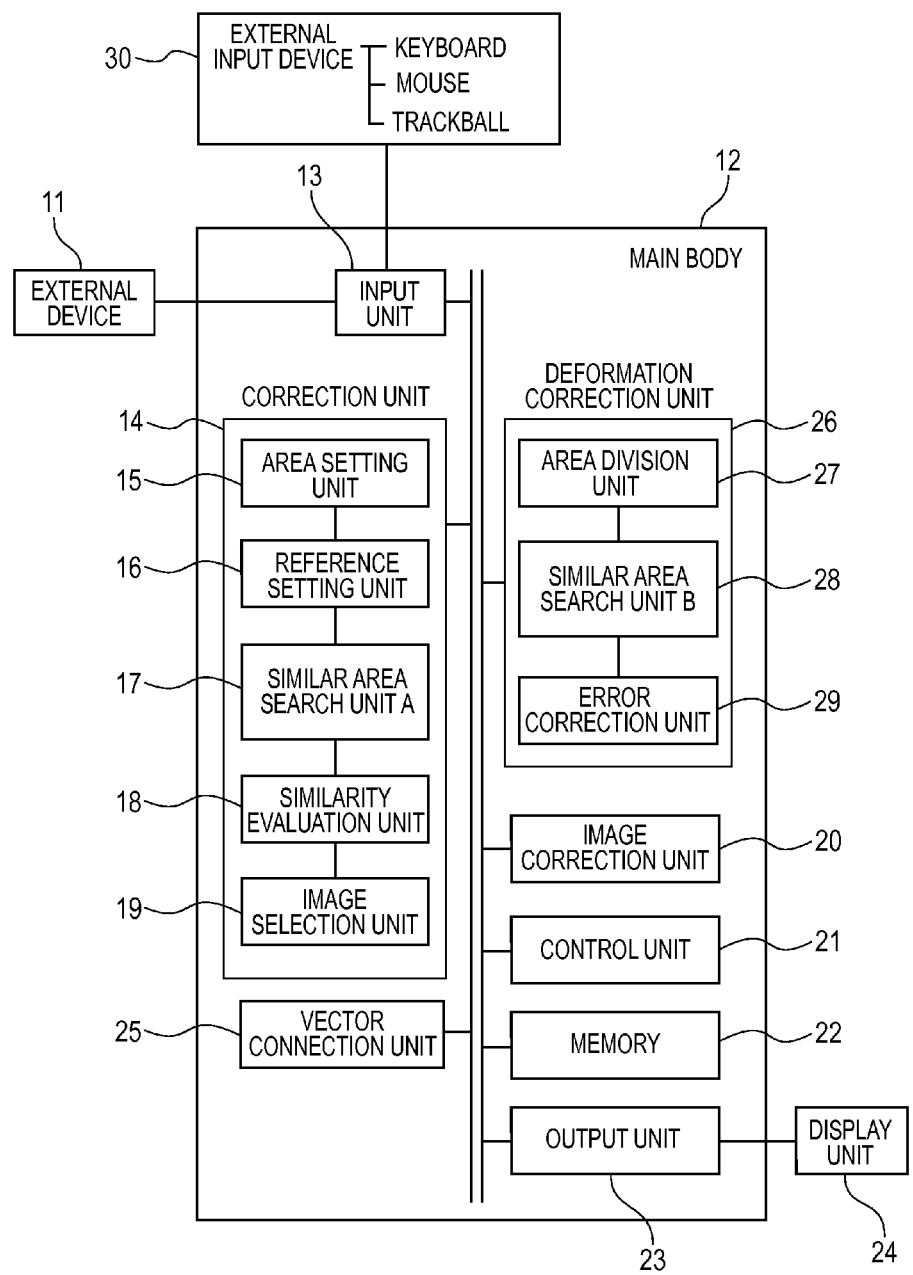
FIG. 12 is a block diagram for showing a configuration example of an image diagnostic device of a second embodiment.

FIG. 12 shows a block diagram of the image diagnostic device of the second embodiment. The deformation correction unit 26 is configured using the area division unit 27, the similar area search unit B28, and the error correction unit 29. The processing content from an entry of the image data from the external device 11 to the correction unit 14 and the vector connection unit 25 is the same as that in the first embodiment, and thus the explanation thereof is omitted. The explanation will be made from the display state shown in FIG. 11 after the corrected image data with the rigid motion of the imaging target corrected is created in the above-described image correction unit 20.

As shown in FIG. 11, the deformation correction button 95 is provided on the display unit 24. When the operator selects the deformation correction button 95 using the external input device 30, the correction vectors corresponding to the image data selected by the image selection unit 19 are output from the memory 22 to the deformation correction unit 26.

Figure 13:
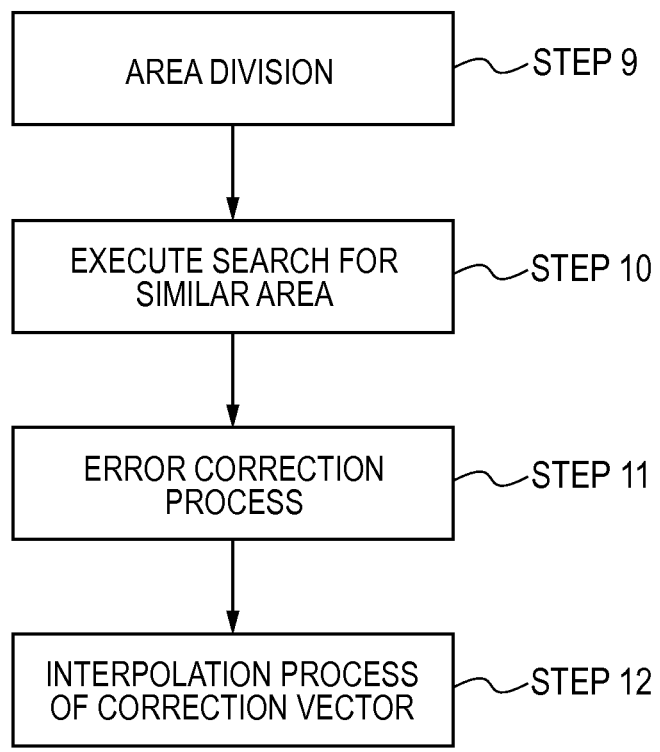
FIG. 13 is a diagram for explaining processing steps of the image diagnostic device of the second embodiment.

Processing steps in the deformation correction unit 26 of the second embodiment are shown in FIG. 13. The processes in the processing steps can be realized by a software process of the CPU that is a processing unit, as similar to the above-described embodiment.

Figure 14:
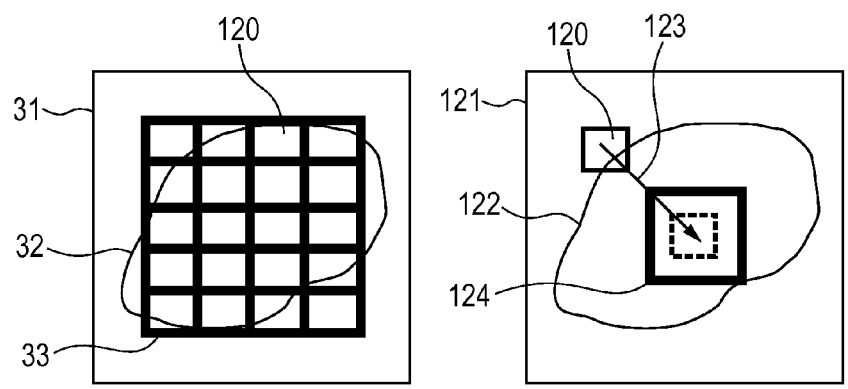
FIG. 14 is a diagram for explaining a search for a similar area according to the second embodiment.

First, the processing area 33 set by the correction unit 14 is further divided into plural divided areas 120 in Step 9 as shown in FIG. 14. The size of the divided areas 120 can be freely set by the operator. However, the minimum size is equal to or larger than the minimum unit configuring the image data. For example, in the case of an ultrasonograph, a speckle size is used as the minimum unit configuring the image data. The speckle size is determined in accordance with imaging conditions such as the aperture, frequency, and depth of a device that irradiates ultrasonic waves. Thus, the size of the divided areas 120 may be differently set depending on locations.

Next, a search for the similar area in Step 10 is performed in the similar area search unit B28. FIG. 14 shows a target image 121 to be corrected and an imaging target 122. The search range is set at a position moved from the position of the divided areas 120 of interest by a correction vector 123 calculated by the correction unit 14. Thus, the value of a search range 124 set by the similar area search unit B28 is smaller than that of the search range set by the correction unit 14. The method of searching for the similar area is the same as that in the first embodiment. However, the process by the edge emphasis filter is not needed because the image data that is not suitable for the correction process is already removed by the correction unit 14.

Next, an error correction process in Step 11 shown in FIG. 13 is performed in the error correction unit 29. The purpose of the process is to correct an error vector detected from the correction vectors of the divided areas calculated in the plural divided areas, and this process is performed for each target image. The error vector is detected by the error correction unit 29 on the basis of a statistical process, an average value (u) and standard deviation ($\sigma$) of the correction vectors calculated in the respective divided areas are calculated, and the error vector that is the correction vector out of range of u±$\sigma$ is corrected using the error vector average value (u).

Next, an interpolation process of the correction vectors is performed in Step 12, and the discontinuity of adjacent correction vectors is removed. The interpolation process is not particularly limited as long as the process is a general process such as a linear interpolation process in accordance with the intervals of the divided areas. When the process in Step 12 is completed, the correction vectors are stored in the memory 22 and at the same time, are output to the image correction unit 20, so that the deformation correction is performed for the image data with the correction process of rigid motion performed.

Figure 15:
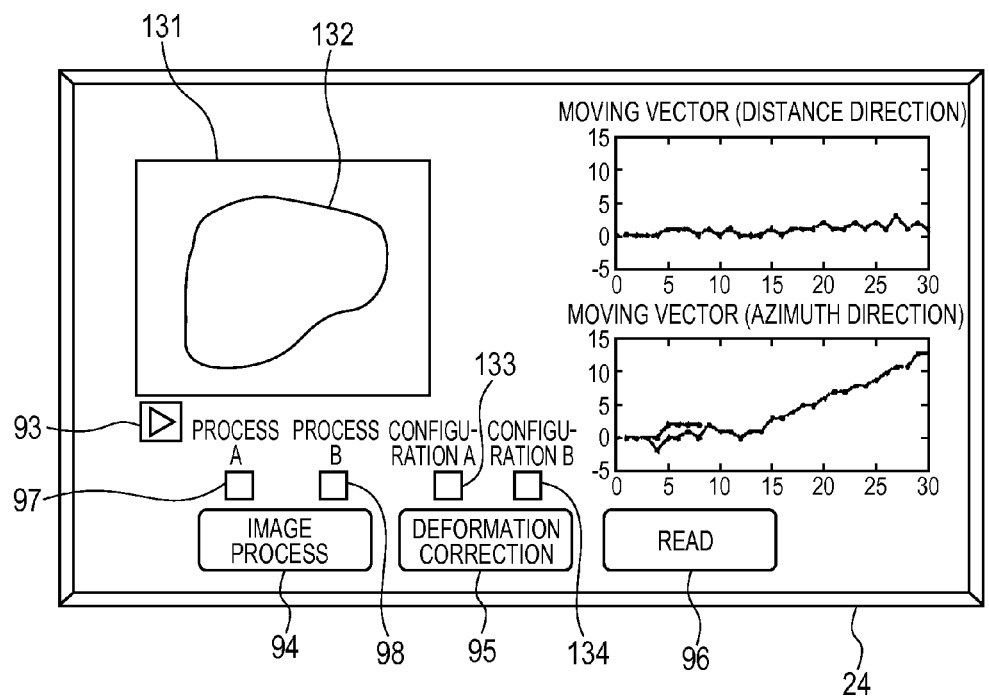
FIG. 15 is a diagram for showing an example of a display configuration of the image diagnostic device of the second embodiment.

As shown in FIG. 15, an example 131 of the corrected image data with the deformation correction performed and an imaging target 132 are displayed on the display unit 24. Further, a configuration A frame 133 and a configuration B frame 134 are further provided above the deformation correction button 95. When the operator inputs a mark into the frame using the external input device 30, the correction vectors calculated in the divided areas are displayed on the corrected image data 131 in various formats.

Figure 16:
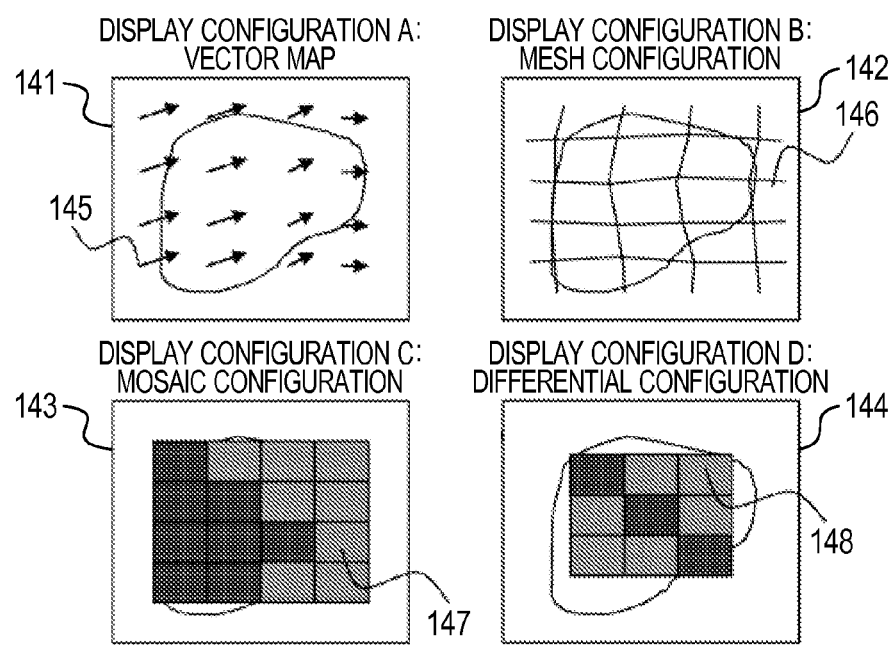
FIG. 16 is a diagram for showing examples of display configurations of correction vectors of the image diagnostic device of the second embodiment.

FIG. 16 shows examples of the display configurations of the display unit 24 in the image diagnostic device of the embodiment. A display configuration A141 is a configuration in which correction vectors 145 calculated in the respective divided areas are displayed using the directions and magnitudes of arrows. A display configuration B142 is a configuration in which each correction vector is displayed using distortion of a mesh 146. A display configuration C143 is a configuration in which each correction vector is displayed using a color density 147. A display configuration D144 is a configuration in which the differential value of each of the adjacent correction vectors is displayed using a color density 148. It is effective in the case where a boundary surface moving in different directions is provided in the imaging target. At least one of the images of these configurations is translucently overlapped with corrected image data 141 to 144 for display. When the reproduction button 93 of FIG. 15 is selected in this stage, the time changes of the corrected image data and the correction vectors can be monitored on moving pictures. It should be noted that the display configuration can be freely changed or added by the operator. Further, the configuration of the display unit 24 can be freely changed by the operator. For example, marks are input into both of the configuration A frame and the configuration B frame, so that images of different configurations can be displayed while being overlapped with each other, or the corrected image data 141 to 144 can be displayed as small thumbnail images.

According to the image diagnostic device of the second embodiment, the correction of the positional shift of the imaging target for the time-series image data can be performed for not only the rigid motion of the imaging target, but also the deformation movement.

As described above in detail, it is possible to provide an image diagnostic device and an image correction method that can realize the high accuracy of correction and can evaluate the reliability of the result as described in various embodiments of the present invention. Further, it is possible to provide an image diagnostic device and an image correction method that can accurately process time-series images using plural pieces of image data to lighten the effects caused by the movement of the imaging target. Furthermore, it is possible to provide an image diagnostic device that can correct the positional shift of the imaging target for the time-series image data to improve the reliability of the correction result. It should be noted that the present invention is not limited to the above-described embodiments, but various modified examples may be included. The above-described embodiments have been described in detail to understandably explain the present invention, and are not necessarily limited to those having the all configurations described above. Further, a part of the configuration in one embodiment can be added to or replaced by another, or deleted.

Further, a part or all of the configurations, functions, processing units, processing means, and the like may be realized by hardware such as designing with an integrated circuit. Further, the configurations, functions, and the like have been described while exemplifying a case in which the configurations, functions, and the like are realized using software by executing programs realizing the respective functions. However, information of programs, tables, files and the like for realizing the functions can be stored into not only the memory, but also a recording device such as a hard disk or an SSD (Solid State Drive), or a recording medium such as an IC card, an SD card, or a DVD. Alternatively, the information can be downloaded or installed via a network or the like as needed basis.

REFERENCE SIGNS LIST 11 external device
12 main body
13 input unit
14 correction unit
15 area setting unit
16 reference setting unit
17 similar area search unit A
18 similarity evaluation unit
19 image selection unit
20 image correction unit
21 control unit
22 memory
23 output unit
24 display unit
25 vector connection unit
26 deformation correction unit
27 area division unit
28 similar area search unit B
29 error correction unit
30 external input device
31 image data
32 imaging target
33 processing area
34 input button
35 correction execution button
41 reference image
43 target image
44 search area
45 position corresponding to processing area
51 similarity value map
52 similarity value distribution map
53 position of minimum value on similarity value map
54 position corresponding to 53 on similarity value distribution map
55 maximum value of similarity value distribution map
61 similarity value map of high reliability example
62 similarity value distribution map of high reliability example
63 similarity value map of low reliability example
64 similarity value distribution map of low reliability example
91 example of corrected image data
92 imaging target
93 reproduction button
94 image processing button
95 deformation correction button
96 read button
97 process A frame
98 process B frame
121 target image in deformation correction unit
122 imaging target
123 correction vector calculated by correction unit
124 search area set by deformation correction unit
133 configuration A frame
134 configuration B frame
141 display configuration A
142 display configuration B
143 display configuration C
144 display configuration D
145 correction vectors of divided areas
146 mesh
147, 148 color density

The invention claimed is:

1. An image diagnostic device that corrects time-series image data, the device comprising:
   a correction unit that selects image data to be corrected from the time-series image data on the basis of a similarity to a processing area in a reference image and outputs correction vectors representing the positional shift of the selected image data, wherein the correction unit comprises:
      a first similar area search unit that searches the image data for an area similar to the processing area in the reference image and outputs a similarity value map indicating similarity values between the processing area and a plurality of areas in the time-series image data;
      a similarity evaluation unit that calculates one or more similarity parameters using the similarity value map and evaluates the reliability of the one or more similarity parameters; and
      an image selection unit that selects the image data used in the image correction unit on the basis of the calculated one or more similarity parameters and the reliability of the one or more similarity parameters;
   an image correction unit that performs a correction process for the image data on the basis of the correction vectors to create corrected image data; and
   a display unit that displays an image on the basis of the corrected image data.

2. The image diagnostic device according to claim 1, wherein the correction unit comprises:
   an area setting unit that sets an area where the correction process is performed for the time-series image data; and
   a reference setting unit that sets the reference image from the time-series image data.

3. The image diagnostic device according to claim 2, wherein the display unit displays time changes of the similarity parameter in the form of a graph or a histogram.

4. The image diagnostic device according to claim 2, wherein the image selection unit compares a threshold value set by an operator for the similarity parameter with the similarity parameter to select the image data to be corrected.

5. The image diagnostic device according to claim 2, wherein the image selection unit calculates an outlier with a statistical process using the average value, the distribution value, or the standard deviation of the similarity parameters, and selects the image data to be corrected by removing the outlier.

6. The image diagnostic device according to claim 2, wherein:
 a vector connection unit is further provided;
 in the case where a plurality of reference images are set, the correction unit calculates the correction vectors and the similarity parameter for each of the plurality of reference images for the image data among the plurality of reference images; and
 the vector connection unit selects the correction vector corresponding to a smaller one of the calculated plurality of similarity parameters to be output to the image correction unit.

7. The image diagnostic device according to claim 2, wherein a deformation correction unit is further provided, and the deformation correction unit includes an area division unit that divides the area where the correction process set by the correction unit is performed to set a plurality of divided areas, a second similar area search unit that searches the plurality of divided areas for the area similar to the reference image to calculate the correction vectors, and an error correction unit that performs error correction for the correction vectors calculated by the second similar area search unit.

8. The image diagnostic device according to claim 7, wherein the second similar area search unit searches for the area similar to the reference image at a position moved by the correction vectors calculated by the similar area search unit.

9. The image diagnostic device according to claim 7, wherein the error correction unit detects a vector of an outlier as an error vector among the correction vectors of the divided areas calculated by the second similar area search unit, and corrects the error vector using the average value of the correction vectors.

10. The image diagnostic device according to claim 7, wherein an external input device is further provided to select whether or not the process of the deformation correction unit is performed.

11. The image diagnostic device according to claim 1, wherein the similarity evaluation unit creates a similarity value distribution map by applying an edge emphasis filter to the similarity value map.

12. The image diagnostic device according to claim 11, wherein the similarity evaluation unit uses, as the similarity parameter, at least one of the maximum value or the minimum value on the similarity value map, the maximum value or the minimum value on the similarity value distribution map, or a distance of a position representing the maximum value or the minimum value calculated on the similarity value map and the similarity value distribution map.

13. The image diagnostic device according to claim 1, wherein the image correction unit further processes an averaging image or a maximum brightness image holding the maximum brightness of each pixel for the plurality of pieces of corrected image data with the correction process performed.

14. An image correction method in which a processing unit corrects time-series image data, wherein the processing unit:
 selects image data to be corrected from the time-series image data on the basis of a similarity to a reference image, wherein selecting image data is determined by:
  searching the time-series image data for an area similar to the processing area in the reference image and outputs a similarity value map indicating similarity values between the processing area and a plurality of areas in the time-series image data;
  calculating one or more similarity parameters using the similarity value map and evaluates the reliability of the one or more similarity parameters; and
  selecting the image data to be corrected on the basis of the calculated one or more similarity parameters and the reliability of the one or more similarity parameters
 calculates correction vectors indicating the positional shift of the selected image data, and
 performs a correction process for the image data on the basis of the correction vectors to create corrected image data.

* * * * *